United States Patent
Gagnon et al.

(10) Patent No.: US 9,770,219 B2
(45) Date of Patent: Sep. 26, 2017

(54) COMPUTED-TOMOGRAPHY APPARATUS INCLUDING DETECTORS WITH DIFFERENT SENSITIVITIES

(71) Applicant: Toshiba Medical Systems Corporation, Otawara-shi (JP)

(72) Inventors: Daniel Gagnon, Twinsburg, OH (US); Miesher L. Rodrigues, Buffalo Grove, IL (US); Yuexing Zhang, Naperville, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 170 days.

(21) Appl. No.: 14/499,939

(22) Filed: Sep. 29, 2014

(65) Prior Publication Data

US 2016/0089091 A1 Mar. 31, 2016

(51) Int. Cl.
*A61B 6/00* (2006.01)
*A61B 6/03* (2006.01)
*A61B 6/06* (2006.01)

(52) U.S. Cl.
CPC .......... *A61B 6/4241* (2013.01); *A61B 6/032* (2013.01); *A61B 6/06* (2013.01); *A61B 6/4266* (2013.01); *A61B 6/482* (2013.01); *A61B 6/4085* (2013.01)

(58) Field of Classification Search
CPC .............................. A61B 6/482; A61B 6/4241
See application file for complete search history.

(56) References Cited

U.S. PATENT DOCUMENTS

| | | | |
|---|---|---|---|
| 7,724,865 B2 * | 5/2010 | Wu | A61B 6/032 378/4 |
| 2013/0034200 A1 * | 2/2013 | Hsieh | A61B 6/03 378/7 |

OTHER PUBLICATIONS

U.S. Appl. No. 14/603,030, filed Jan. 22, 2015, Zhang, et al.

* cited by examiner

*Primary Examiner* — Hoon Song
(74) *Attorney, Agent, or Firm* — Oblon, McClelland, Maier & Neustadt, L.L.P.

(57) ABSTRACT

A computed-tomography (CT) apparatus including a CT scanner including a rotating X-ray source, and a plurality of photon-counting detectors (PCDs) arranged in a fixed detector ring to capture incident X-ray photons emitted from the X-ray source. The plurality of PCDs includes a first plurality of first PCDs, each first PCD having a first collimator on a surface of the first PCD to block X-ray photons emitted from the X-ray source, the first collimator having openings of a first size, and a second plurality of second PCDs, each second PCD having a second collimator on a surface of the second PCD to block the X-ray photons emitted from the X-ray source, the second collimator having openings of a second size, the first size being different from the second size.

7 Claims, 6 Drawing Sheets

COMPUTED-TOMOGRAPHY APPARATUS INCLUDING DETECTORS WITH DIFFERENT SENSITIVITIES

CROSS-REFERENCE TO RELATED APPLICATIONS

The present application is related to application Ser. No. 14/092,998, filed Nov. 28, 2013 and application Ser. No. 13/896,949, filed May 17, 2013, the entire contents of each of which are incorporated herein by reference.

FIELD

Embodiments described herein relate to a computed-tomography (CT) apparatus including photon-counting detectors having different sensitivities.

BACKGROUND

Direct-conversion photon-counting detectors (PCDs) (for example, CdZnTe or CdTe) suffer from polarization (space-charge build-up in the semiconductor sensor) and electronics pile-up at high X-ray flux levels typically used in CT imaging. A detector-side collimator with small slit-shape openings is used to mitigate this problem. The detector-side collimator has a fixed slit opening size, which is optimized for a certain flux level.

However, the X-ray flux levels in typical CT imaging vary dramatically within a scan. Such a flux level variation depends upon the patient size, shape, and anatomy, as well as the wedge profile. A fixed-size detector-side collimator may be either inadequate in preventing polarization under high flux (opening too large) or insensitive to low-flux conditions (opening too small).

BRIEF DESCRIPTION OF THE DRAWINGS

The disclosure will be better understood from reading the description which follows and from examining the accompanying figures. These figures are provided solely as non-limiting examples of the embodiments. In the drawings.

DETAILED DESCRIPTION

Figure 1:
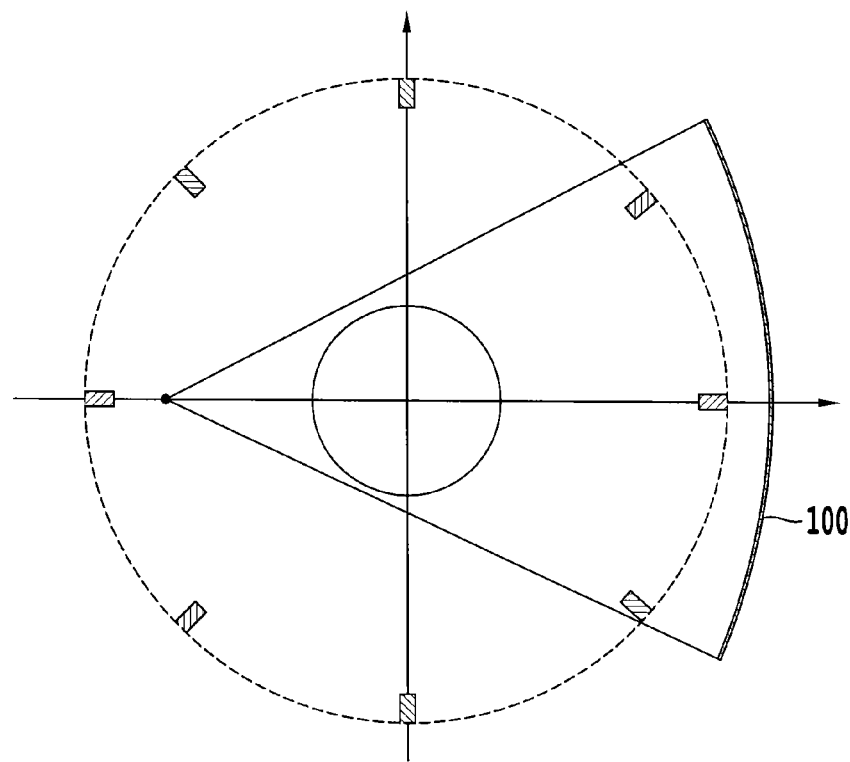
FIG. 1 illustrates a CT imaging system.

In one embodiment, a CT scanner includes a rotating X-ray source, and a plurality of photon-counting detectors (PCDs) arranged in a fixed detector ring to capture incident X-ray photons emitted from the X-ray source, wherein the plurality of PCDs includes a first plurality of first PCDs, each first PCD having a first collimator on a surface of the first PCD to block X-ray photons emitted from the X-ray source, the first collimator having openings of a first size, and a second plurality of second PCDs, each second PCD having a second collimator on a surface of the second PCD to block the X-ray photons emitted from the X-ray source, the second collimator having openings of a second size, the first size being different from the second size.

In one embodiment, each of the first plurality of first PCDs is arranged in an alternating fashion with each of the second plurality of second PCDs in a circumferential direction around the X-ray source.

In one embodiment, the first collimator includes a plurality of first collimator elements, the second collimator includes a plurality of second collimator elements, and a first collimator element of the first collimator elements has a different width than a second collimator element of the second collimator elements.

In one embodiment, the first size is larger than the second size, and the first plurality of PCDs exhibit higher sensitivity than the second plurality of PCDs.

In one embodiment, a CT apparatus includes a CT scanner including a rotating X-ray source, and a plurality of PCDs arranged in a fixed detector ring to capture incident X-ray photons emitted from the X-ray source, wherein each of the PCDs includes a collimator arranged on a surface of each of the PCDs to provide openings of at least two different sizes in an axial direction.

In one embodiment, the collimator includes a plurality of collimator elements, and at least one collimator element of the plurality of collimator elements has a different width than another collimator of the plurality of collimator elements.

In one embodiment, a CT apparatus includes a CT scanner including a rotating X-ray source, and a plurality of PCDs arranged in a fixed detector ring to capture incident X-ray photons emitted from the X-ray source, each PCD including a plurality of collimators each arranged on a surface of the PCD to block X-ray photons emitted from the X-ray source, wherein each PCD includes a first crystal and a second crystal with a gap therebetween, and the first crystal and the second crystal in each PCD are arranged so that the gap is not in a same transaxial plane for PCDs adjacent in the circumferential direction.

In one embodiment, the first crystal and the second crystal have different lengths.

In one embodiment, the first crystal is shorter than the second crystal.

In one embodiment, the gap between the first crystal and the second crystal of each PCD is of a same size.

A CT apparatus includes the detectors described herein, as well as additional mechanical and electrical components such as a gantry motor and a controller to control the rotation of the gantry, control the X-ray source, and control a patient bed. The CT apparatus also includes a data acquisition system and a (reconstruction) processor to generate CT images based on the projection data acquired by the data acquisition system. The processor and data acquisition system make use of a memory, which is configured to store e.g., data obtained from the detector and reconstructed images.

FIG. 1 illustrates a sparse spectral CT imaging system that includes stationary, sparse PCDs and a rotating X-ray source. The source trajectory may be inside or outside the ring defined by the PCDs.

Figure 2:
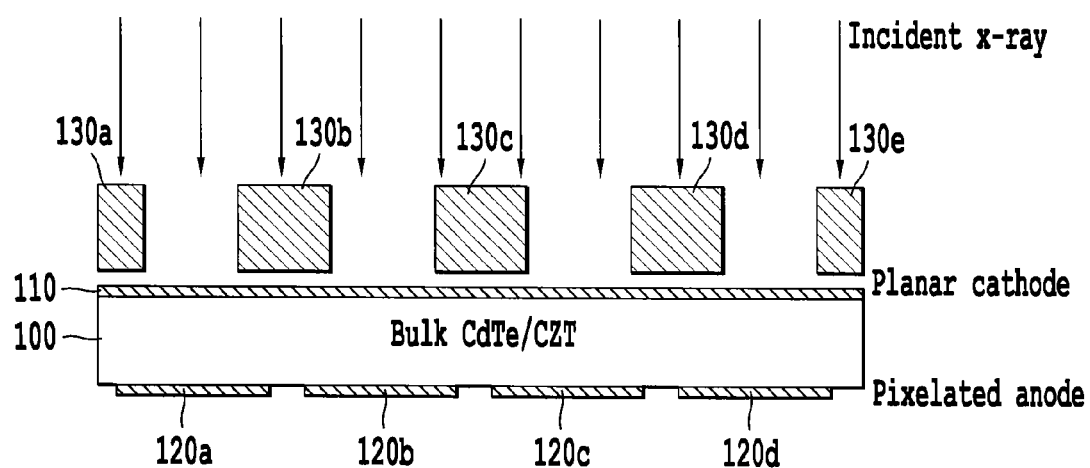
FIG. 2 illustrates an exemplary embodiment of a photon-counting detector (PCD) with collimators.

FIG. 2 illustrates one embodiment of a PCD with a collimator that includes a plurality of collimator elements 130a-130e. As illustrated in FIG. 2, PCD 100 includes pixelated anodes 120a to 120d and a planar cathode 110. In one embodiment, each of pixelated anodes 120a-120d corresponds to an individual pixel. In some embodiments, the PCD 100 is a semiconductor PCD made of a continuous bulk material such as cadmium telluride (CdTe) or cadmium zinc telluride (CZT). As illustrated in FIG. 2, collimator elements 130a-130e are positioned on the cathode side of the PCD 100. In some embodiments, the collimator elements 130a to 130e are provided on the edges of each pixel. In this regard, the collimator elements block out most, but not all, incident X-rays from hitting the edges of the pixels so that only the centers of the pixels 120a-120d receive the incident X-rays.

Accordingly, as illustrated in FIG. 2, the installed collimator with collimator elements 130a-130e separate individual detector channels/pixels. In one embodiment, each of the collimator elements 130a-130e is part of a mask that is overlaid on the cathode side of the PCD. In another embodiment, 10%-60% of the whole cathode is covered by the collimator elements, depending on the amount of flux incident on the PCD.

The present embodiments use variable collimator openings to improve sensitivity and dynamic range. In one embodiment, PCDs with collimator openings of different sizes are used in an "intertwined" fashion along the tangential direction (z-direction, along the length of the patient bed) in the ring configuration. Alternatively, in one embodiment, collimator openings of different sizes are implemented on the same detector element (applies to larger slice thickness).

In one embodiment, collimator openings can be on the order of tens or hundreds of micrometers (μm). The particular collimator openings can be determined according to clinical scan X-ray flux levels. In one embodiment, 50 μm to about 100 μm collimator openings can be used for higher incident X-ray photon rates, while 200 μm to about 300 μm collimator openings can be used for lower incident X-ray photon rates. In one embodiment, collimator openings can vary in size from 50 μm to about 500 μm.

Figure 3:
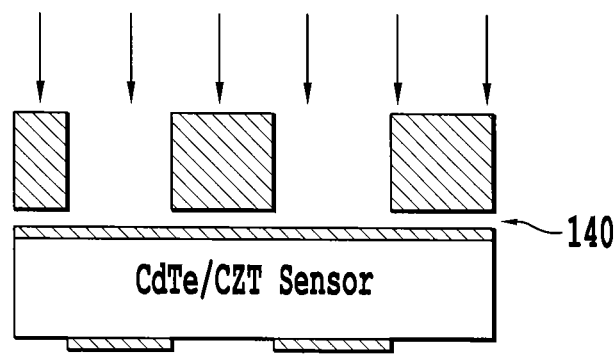
FIG. 3 illustrates one embodiment of a PCD with a larger collimator opening size.

FIG. 3 illustrates one embodiment of a PCD with a relatively larger collimator opening size (collectively referred to as element 140 in FIG. 3). Such a configuration provides higher sensitivity and a smaller dynamic range.

Figure 4:
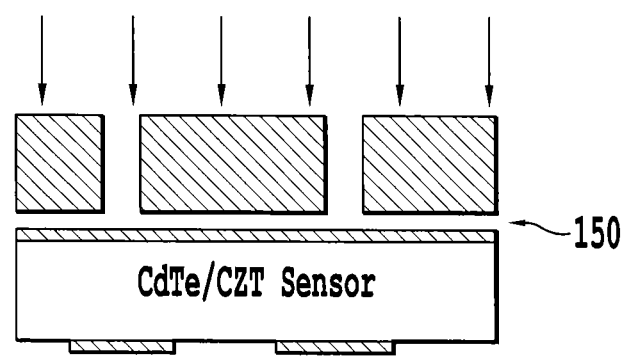
FIG. 4 illustrates one embodiment of a PCD with a smaller collimator opening size.

FIG. 4 illustrates one embodiment of a PCD with a relatively smaller collimator opening size (collectively referred to as element 150 in FIG. 4). Such a configuration provides lower sensitivity and a larger dynamic range. Note that, as illustrated in the figures, the blocking portions (collimator elements) of the collimator illustrated in FIG. 3 are smaller (have a smaller width) than the blocking portions (collimator elements) of the collimator illustrated in FIG. 4.

Figure 5:
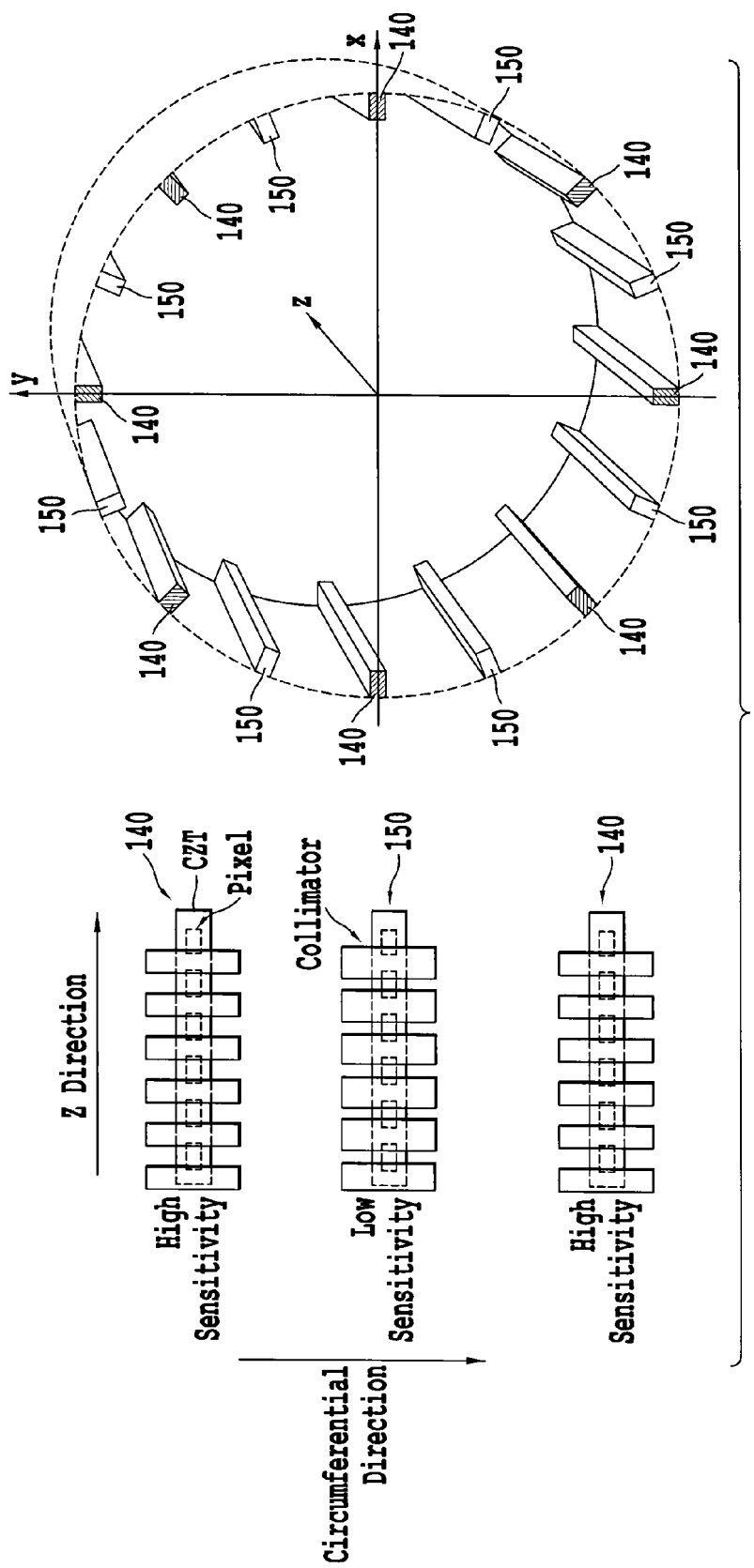
FIG. 5 illustrates an embodiment with an arrangement in which low- and high-sensitivity collimators are alternated circumferentially around a detector ring.

FIG. 5 illustrates an embodiment with an arrangement in which low- and high-sensitivity collimators are alternated circumferentially around the detector ring, such that no PCDs with the same-size collimator openings are located adjacent to each other around the detector ring. In one embodiment, the detector ring is a fourth-generation detector ring including sparsely distributed, fixed PCDs.

Such an arrangement provides the advantage of having an optimal compromise between sensitivity and dynamic range while allowing at least one detector to survive the flux, and also provides continuity of measurement around the object. Note that the z-direction extends through the detector ring (i.e., into the page, along the length of the patient bed). Note also that the entire ring of FIG. 5 exhibits alternating 'high sensitivity' with 'low sensitivity' in the circumferential direction because detectors 140 alternate with detectors 150 around the entire ring.

Figure 6:
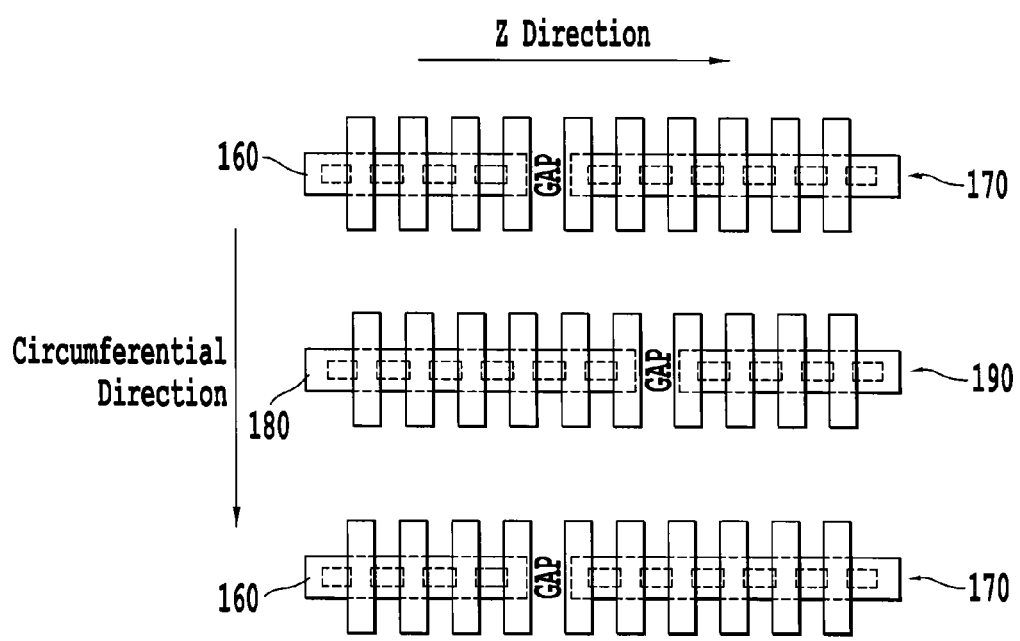
FIG. 6 illustrates an embodiment with an arrangement in which longer and shorter PCDs along the z-axis are alternated circumferentially around the detector ring.

FIG. 6 illustrates an embodiment in which longer and shorter monolithic crystals arranged in the z direction are alternated circumferentially around the detector ring so that the "seam" between crystals (i.e., the gap illustrated in the figure) does not always appear in the same transaxial plane. Thus, the gaps between consecutive crystals in PCDs are at alternating z locations around the ring. In other words, the gap between crystal/PCD 160 and crystal/PCD 170 is at a different location than the gap between crystal/PCD 180 and crystal/PCD 190. Note that the gap is not a physical gap, but rather a region in which no data is being collected due to the absence of a pixel.

Such arrangement applies to "wide-cone" multi-slice scans, where more than one pixelated detector sensor is needed to achieve large z coverage.

To briefly discuss wide-cone scans, a 16-slice scan is generally not considered a wide-cone scan, while a 320-slice scan is considered to be a wide-cone scan. Thus, using a 320-slice scanner (such as the Toshiba® Aquilion One), one can image a larger portion of the patient in a single scan, using more detector elements in the z-direction, and at the same time opening the cone angle of the X-ray tube accordingly. The benefit of using wide-cone scans is related to the overall scan time for some exams (for example, in cardiac imaging where the object being imaged is in constant motion).

Thus, "wide-cone" refers to a large coverage in the z-direction. When the coverage is large, it becomes difficult to have a long, continuous detector element. As a result, the gap discussed above is introduced.

Note that crystals/PCDs 160-190 in the embodiment of FIG. 6 are illustrated as having the same-sized collimator openings. However, in one embodiment, the crystals/PCDs may have different collimator opening sizes and/or different collimator element widths, as discussed above with respect to FIGS. 3-5.

Further, as long as the gaps alternate, the pixels from PCDS 160 and 170 need not be aligned with pixels from the PCDs 180 and 190.

Note that, in one embodiment, the anodes can be placed at the end of the PCDs 160, 170, 180, and 190, such that the gap is between the anodes, and the collimators on the ends of the PCDs 160, 170, 180, and 190 would cover the gap. In one embodiment, the gap can be larger than the blocking portion of the collimator (depending on the blockage fraction).

Figure 7:
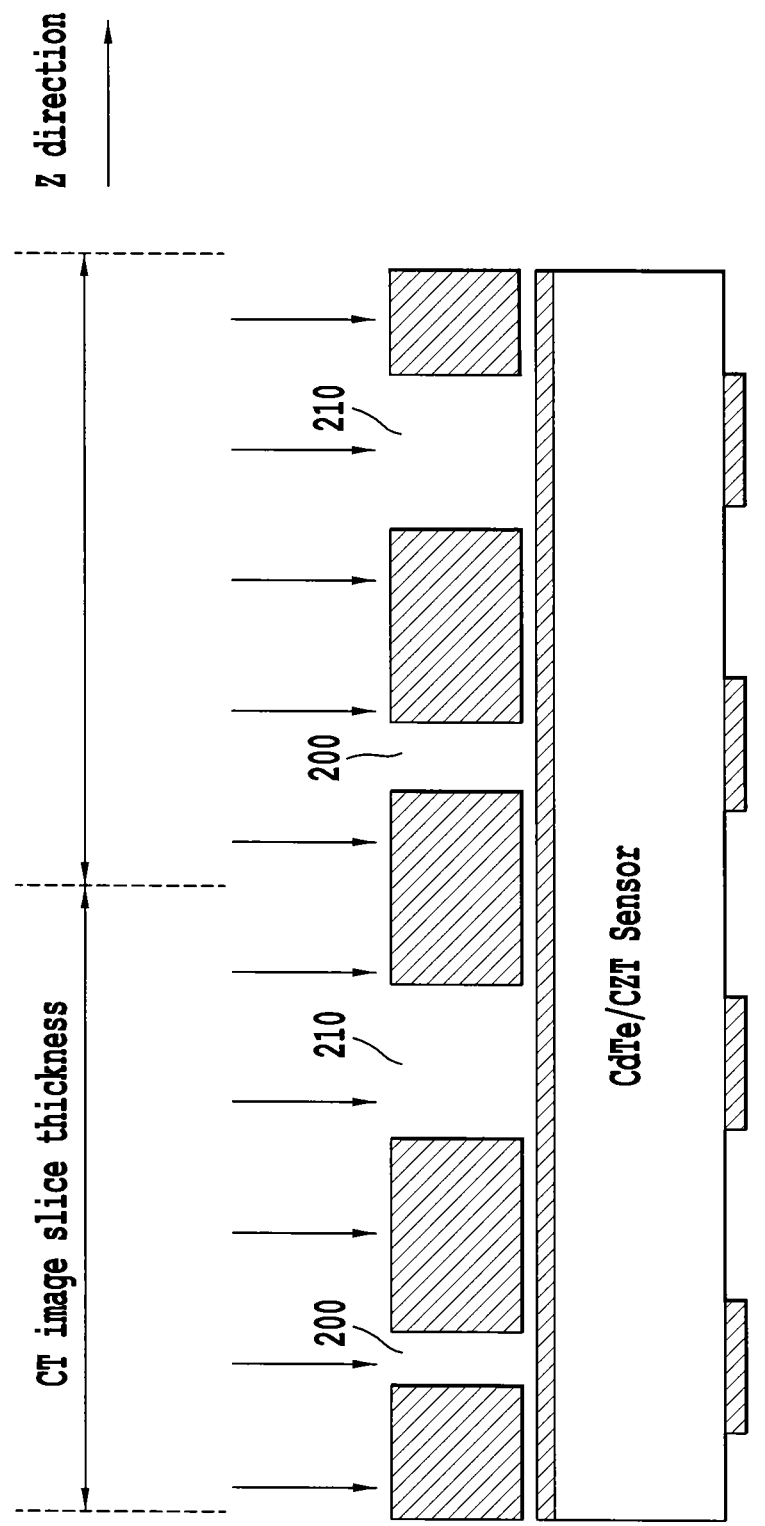
FIG. 7 illustrates an embodiment with an arrangement in which the opening size between each collimator element alternates from a smaller opening size to a larger opening size.

FIG. 7 illustrates an embodiment of alternating pixels of high sensitivity (large collimator opening) and low sensitivity (small collimator opening) along the z-direction for a given PCD. In other words, in the embodiment illustrated in FIG. 7, adjacent openings within the same collimator alternate between a smaller opening size and a larger opening size (see openings 200 and 210 in FIG. 7). Similarly to the embodiment of FIG. 5, the PCD shown in FIG. 7 is arranged at a fixed position in the detector ring.

Note that, in one embodiment, the widths of the collimator elements can also vary along the PCD. In this embodiment, one pair of high- and low-sensitivity pixels can be used to sample every slice. At low flux, data from the high-sensitivity pixels are mostly used. At high flux, the low-sensitivity pixels can survive the flux and provide useful data. Note that alternating high- and low-sensitivity pixels along the PCD, as discussed with respect to FIG. 7, allows for thicker slices to be imaged.

Note that a pattern (of higher and lower sensitivity) in the z-direction can be made to accommodate a continuous variation (as to compensate for an X-ray beam shape, for example) or alternating to cover a better dynamic range in the z-direction (as is the case for circumferential sampling), or a combination of the two.

For example, in one embodiment, the PCD shown in FIG. 7 can alternate around the detector ring with a PCD having alternating pixels of low sensitivity (small collimator opening) and high sensitivity (large collimator opening) along the z-direction. In other words, in the detector ring, a first PCD can have high-, low-, high-, low-, high-sensitivity, an immediately adjacent second PCD can have a low-, high-, low-, high-sensitivity, and an immediately adjacent third PCD can have a high-, low-, high-sensitivity. Alternatively, this arrangement may be reversed.

With any of the embodiments discussed herein, detectors of different sensitivity can require different electronics settings. For example, different application specific integrated circuit (ASIC) peaking times can be used for pixels having different collimator opening sizes. In other words, the ASIC peaking times can be adjusted based on the sensitivity of the pixel and the size of the collimator openings. This will reduce electronic noise and pile-up. Other electronics settings for detectors of different sensitivities can also be different.

Note that, generally, a longer peaking time is desirable for reducing electronic noise. Pile-up increases when using a longer peaking time, so there is a trade-off between pile-up and noise. Having different ASIC peaking times has the advantage of optimizing both the noise and pile-up levels in the system. The transition between useful counts in low-sensitivity pixels and useful counts in the high-sensitivity pixels is continuous. Thus, at higher incident X-ray rates, data from high-sensitivity pixels can still be useful if shorter peaking times are used in high-sensitivity pixels compared with low-sensitivity pixels.

As discussed above, the embodiments described herein address the X-ray flux dynamic range limitation associated with fixed-size detector-side collimators. The embodiments discussed herein prevent space-charge polarization while maintaining a wide flux dynamic range for at least a portion of the detector ring.

The embodiments described herein also address the application of this technology in a wide-cone scanner that requires a longer crystal with alternating 'gaps' therebetween.

Figure 8:
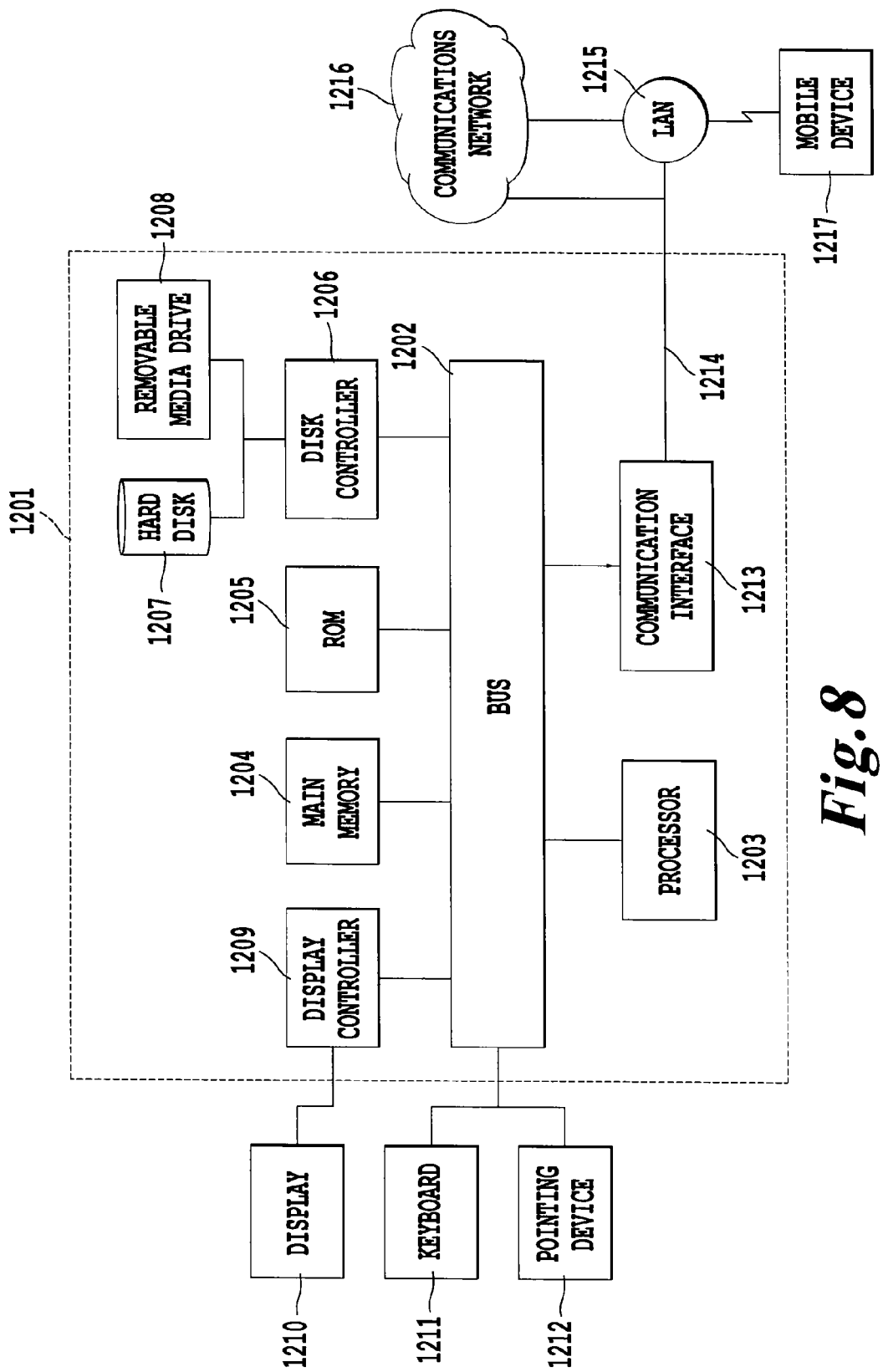
FIG. 8 illustrates a computer system upon which features of a CT apparatus may be implemented.

As noted above, various features of the CT apparatus may be implemented by a computer system (or programmable logic). FIG. 8 illustrates such a computer system 1201. The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The processor 1203 executes one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
a CT scanner including a rotating X-ray source; and
a plurality of photon-counting detectors (PCDs) arranged in a fixed detector ring to capture incident X-ray photons emitted from the X-ray source, wherein
the plurality of PCDs includes
a first plurality of first PCDs, each first PCD having a first collimator on a surface of the first PCD to block X-ray photons emitted from the X-ray source, the first collimator having openings of a first size, and
a second plurality of second PCDs, each second PCD having a second collimator on a surface of the second PCD to block the X-ray photons emitted from the X-ray source, the second collimator having openings of a second size, the first size being different from the second size due to a difference between a first opening of the first collimator for each pixel and a second opening of the second collimator for each pixel.

2. The CT apparatus of claim 1, wherein
each of the first plurality of first PCDs is arranged in an alternating fashion with each of the second plurality of second PCDs in a circumferential direction around the X-ray source.

3. The CT apparatus of claim 1, wherein
the first collimator includes a plurality of first collimator elements,
the second collimator includes a plurality of second collimator elements, and
a first collimator element of the first collimator elements has a different width than a second collimator element of the second collimator elements.

4. The CT apparatus of claim 1, wherein
the first size is larger than the second size, and
the first plurality of PCDs exhibit higher sensitivity than the second plurality of PCDs.

5. A computed-tomography (CT) apparatus, comprising:
a CT scanner including a rotating X-ray source; and
a plurality of photon-counting detectors (PCDs) arranged in a fixed detector ring to capture incident X-ray photons emitted from the X-ray source, wherein
each of the PCDs includes a collimator arranged on a surface of each of the PCDs to provide openings of at least two different sizes for two different pixels in an axial direction.

6. The CT apparatus of claim 5, wherein
the collimator includes a plurality of collimator elements, and
at least one collimator element of the plurality of collimator elements has a different width than another collimator of the plurality of collimator elements.

7. The CT apparatus of claim 1, wherein the plurality of PCDs are evenly spaced along an entirety of an inner surface of the fixed detector ring.

\* \* \* \* \*